(12) United States Patent
Dubois

(10) Patent No.: US 7,531,699 B2
(45) Date of Patent: May 12, 2009

(54) ACROLEIN PREPARATION METHOD

(75) Inventor: Jean-Luc Dubois, Millery (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 12/162,691

(22) PCT Filed: Feb. 6, 2007

(86) PCT No.: PCT/FR2007/050757

§ 371 (c)(1),
(2), (4) Date: Jul. 30, 2008

(87) PCT Pub. No.: WO2007/090990

PCT Pub. Date: Aug. 16, 2007

(65) Prior Publication Data

US 2008/0319233 A1 Dec. 25, 2008

(30) Foreign Application Priority Data

Feb. 7, 2006 (FR) .................. 06 01059

(51) Int. Cl.
*C07C 45/35* (2006.01)
*C07C 45/52* (2006.01)
(52) U.S. Cl. ..................... 568/476; 568/485
(58) Field of Classification Search .............. 568/476, 568/485
See application file for complete search history.

(56) References Cited

U.S. PATENT DOCUMENTS

| 2,558,520 | A | 6/1951 | Hoyt et al. |
| 5,218,146 | A | 6/1993 | Takata et al. |
| 5,387,720 | A | 2/1995 | Neher et al. |
| 6,080,898 | A | 6/2000 | Drent et al. |
| 7,268,254 | B2 | 9/2007 | Olbert et al. |
| 2004/0220434 | A1 | 11/2004 | Brophy et al. |

FOREIGN PATENT DOCUMENTS

| EP | 995491 | 4/2000 |
| EP | 1147807 | 10/2001 |
| FR | 695931 | 5/1930 |
| GB | 1152215 | 5/1969 |

OTHER PUBLICATIONS

Edition Technip; Marcilly, C.; 200;, p. 71, 1975.

*Primary Examiner*—Sikarl A Witherspoon
(74) *Attorney, Agent, or Firm*—Steven D. Boyd

(57) ABSTRACT

The invention relates to a method for preparing acrolein from propylene, consisting of a first glycerol dehydration step preformed in the presence of a gas containing propylene and, more specifically, in the presence of the reaction gas originating from the propylene to acrolein oxidation step. The inventive method enables the use, in part, of renewable raw material, while increasing acrolein production.

9 Claims, 3 Drawing Sheets

ACROLEIN PREPARATION METHOD

TECHNICAL FIELD

The present invention relates to a process for the preparation of acrolein from propylene, comprising a stage of dehydration of glycerol in the presence of a propylene-comprising gas and more particularly in the presence of the reaction gas resulting from the stage of oxidation of the propylene to give acrolein.

BACKGROUND OF THE INVENTION

The process for the production of acrolein most commonly used is based on the gas-phase catalytic oxidation reaction of propylene by atmospheric oxygen, such as described, for example, in the document Techniques de l'ingénieur, traité Génie des procédés [Techniques for the Engineer, Process Engineering Treatise], J 6 100 1-4. The acrolein thus obtained can either be incorporated directly in a two-stage process for the manufacture of acrylic acid from propylene in the gas phase or be used as synthetic intermediate. Acrolein is in particular a key intermediate in the synthesis of methionine, a synthetic amino acid used as animal food supplement which has emerged as a substitute for fishmeal. Acrolein also has numerous other applications in preparing derivatives which can be synthesized on the actual site of production of the acrolein, thus limiting the storage and transportation of this toxic chemical product.

In a certain number of cases, it may be advantageous to be able to increase the acrolein production capacities of existing units.

The production of acrolein is highly dependent on the starting material, propylene. Propylene, obtained by steam cracking or catalytic cracking of petroleum fractions, has the disadvantage of contributing to the increase in the greenhouse effect, as a result of its fossil origin. Furthermore, propylene resources may become limited.

It thus appears particularly advantageous to be able to increase the productive output of acrolein while reducing dependence on a fossil resource.

It has been known for a long time that glycerol can contribute to the production of acrolein. Glycerol results from the methanolysis of vegetable oils, at the same time as the methyl esters, which are themselves employed in particular as fuels in diesel oil and heating oil. This is a natural product which enjoys a "green" aura, is available in a large amount and can be stored and transported without difficulty.

Numerous studies are devoted to giving an economic value to glycerol according to its degree of purity, and the dehydration of glycerol to give acrolein is one of the routes envisaged.

The reaction involved in producing acrolein from glycerol is:

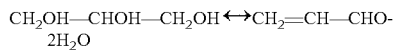

Generally, the hydration reaction is promoted at low temperatures and the dehydration reaction is promoted at high temperatures. In order to obtain acrolein, it is thus necessary to employ a satisfactory temperature and/or a partial vacuum in order to displace the reaction. The reaction can be carried out in the liquid phase or in the gas phase. This type of reaction is known to be catalyzed by acids. Various processes for the synthesis of acrolein from glycerol are described in the prior art; mention may in particular be made of the documents FR 695931, U.S. Pat. No. 2,558,520, WO 99/05085 and U.S. Pat. No. 5,387,720.

It has now been found that the reaction for the dehydration of glycerol to give acrolein can be carried out in the presence of a propylene-comprising gas. It is thus advantageous to introduce glycerol into the process for the gas-phase catalytic oxidation of propylene, which makes it possible to use a renewable starting material while increasing the production of acrolein. Such a process becomes particularly advantageous for the synthesis of methionine, which can then be said to be "obtained from biomass". This is because the methionine, when it is used in the feeding of animals, is rapidly metabolized and the carbon dioxide gas, which is reencountered in the atmosphere, contributes to increasing the greenhouse effect. If the acrolein is obtained partially from a renewable starting material, such as the glycerol originating from vegetable oil, the $CO_2$ emissions no longer entirely participate in the balance of the process as they offset the carbon dioxide gas used by the biomass for its growth; there is thus a limitation on the increase in the greenhouse effect. Such a process then corresponds to the criteria associated with the new concept of "green chemistry" in the more general context of sustainable development.

SUMMARY OF THE INVENTION

The subject matter of the present invention is thus a process for the preparation of acrolein by oxidation of propylene comprising a stage of dehydration of glycerol in the presence of a propylene-comprising gas. The dehydration reaction of glycerol can be carried out in the presence of the gas mixture which feeds the reactor for the oxidation of the propylene, generally composed of propylene, steam, an inert gas, which can be nitrogen or argon, and molecular oxygen or a gas comprising molecular oxygen.

According to a preferred embodiment of the invention, the stage of dehydration of the glycerol is carried out in the presence of the reaction gas resulting from the stage of oxidation of the propylene to give acrolein. This reaction gas is generally composed of a mixture of the unreacted gases (unconverted propylene, propane initially present in the propylene, inert gas, steam, oxygen, CO, $CO_2$), of acrolein produced and of various byproducts, such as acrylic acid, acetic acid and other minor compounds.

Without the Inventor being committed to any one explanation, it believes that the stage of dehydration of the glycerol makes it possible to cool the reaction gases resulting from the stage of oxidation of the propylene to give acrolein.

This is because, in the reaction for the oxidation of propylene to give acrolein, the reaction gases exit from the reaction region at a high temperature, the reaction for the oxidation of propylene being exothermic. It is necessary to cool these reactions gases in order to recover the acrolein. In a process for the preparation of acrylic acid from propylene in two stages, it is also necessary to cool the reaction gases resulting from the first stage of oxidation of the propylene to give acrolein before entering the second stage of oxidation of the acrolein to give acrylic acid as the reaction for the oxidation of the acrolein to give acrylic acid takes place at a lower temperature than the reaction for the oxidation of the propylene to give acrolein. Furthermore, the acrolein can self ignite at high temperatures, resulting in losses in yields.

This cooling is generally obtained by virtue of a heat exchanger placed downstream of the catalytic region. The same effect can, in all or part, be obtained by virtue of the use of an endothermic reaction, such as the dehydration of glycerol. In the present invention, the dehydration reaction of glycerol exhibits the advantage of resulting in the same main reaction product (acrolein) as the reaction for the oxidation of propylene. This thus results in an increase in the productive output of acrolein while efficiently recovering the heat from the oxidation reaction.

Other characteristics and advantages of the invention will emerge more clearly on reading the description which follows, with reference to the appended figures, in which:

DETAILED DESCRIPTION OF THE INVENTION

Figure 1:
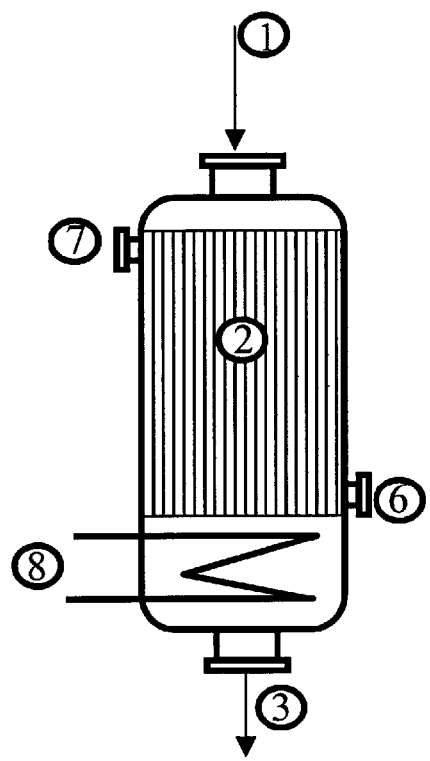
FIG. 1 diagrammatically represents a conventional reactor for the oxidation of propylene to give acrolein, FIGS. 2, 3, 4 and 5 diagrammatically represent different configurations of reactors for the oxidation of propylene to give acrolein corresponding to embodiments of the process according to the invention.

In the process of the invention, the stage of dehydration of glycerol is carried out in the gas phase in the presence of a catalyst at a temperature ranging from 150° C. to 500° C., preferably between 250° C. and 350° C., and a pressure between 1 and 5 bar.

The stage of dehydration of glycerol can be carried out upstream of the reaction for the catalytic oxidation of the propylene in the presence of the feed gas comprising the propylene or downstream of the reaction for the catalytic oxidation of the propylene in the presence of the gas mixture resulting from this reaction. It can be incorporated directly in the oxidation reactor or can be carried out in a reactor placed immediately upstream or downstream of the reactor for the oxidation of the propylene. As the dehydration reaction is slightly endothermic, it is not necessary to have a multitubular bed for this reaction. A conventional fixed bed may be suitable, and also a configuration in modules (sheets or pans). The modules exhibit the advantage of being able to be easily charged and discharged when the catalyst is deactivated.

The catalysts which are suitable are homogeneous or multiphase materials which are insoluble in the reaction medium and which have a Hammett acidity, recorded as $H_0$, of less than +2. As indicated in U.S. Pat. No. 5,387,720, which refers to the article by K. Tanabe et al. in "Studies in Surface Science and Catalysis", Vol. 51, 1989, chap. 1 and 2, the Hammett acidity is determined by amine titration using indicators or by adsorption of a base in the gas phase. The catalysts corresponding to the criterion of $H_0$ acidity of less than +2 can be chosen from siliceous materials (natural or synthetic) or acid zeolites; inorganic supports, such as oxides, covered with mono-, di-, tri- or polyacidic inorganic acids; oxides or mixed oxides; or heteropolyacids.

Advantageously, the catalysts are chosen from zeolites, Nafion® composites (based on sulfonic acid of fluoropolymers), chlorinated aluminas, phosphotungstic and/or silicotungstic acids and acid salts, and various solids of the type formed of metal oxides, such as tantalum oxide $Ta_2O_5$, niobium oxide $Nb_2O_5$, alumina $Al_2O_3$, titanium oxide $TiO_2$, zirconia $ZrO_2$, tin oxide $SnO_2$, silica $SiO_2$ or silicoaluminate $SiO_2/Al_2O_3$, impregnated with acid functional groups, such as borate $BO_3$, sulfate $SO_4$, tungstate $WO_3$, phosphate $PO_4$, silicate $SiO_2$ or molybdate $MoO_3$ acid functional groups. According to the literature data, these catalysts always have a Hammett acidity $H_0$ of less than +2.

The preferred catalysts are sulfated zirconias, phosphated zirconias, tungstated zirconias, silica zirconias, sulfated titanium or tin oxides, or phosphated aluminas or silicas.

These catalysts all have a Hammett acidity $H_0$ of less than +2; the acidity $H_0$ can then vary to a large extent, down to values which can reach −20 in the reference scale with Hammett indicators. The table given on page 71 of the publication on acid/base catalysis (C. Marcilly), Vol. 1, in Editions Technip (ISBN No. 2-7108-0841-2), illustrates examples of solid catalysts in this acidity range.

The glycerol is used pure or in the form of a concentrated or dilute aqueous solution. Advantageously, use may be made of an aqueous glycerol solution with a concentration ranging from 10% to 100% by weight. In the embodiment of the invention where the stage of dehydration of glycerol is carried out upstream of the reaction for the catalytic oxidation of the propylene, use may be made of an aqueous glycerol solution, preferably with a concentration ranging from 10% to 50% by weight, more particularly from 15% to 30% by weight. The concentration must not be too high in order to avoid side reactions, such as the formation of glycerol ethers or reactions between the acrolein produced and the glycerol. Furthermore, the glycerol solution must not be too dilute due to the energy cost resulting from the evaporation of the aqueous glycerol solution. In the embodiment of the invention where the stage of dehydration of glycerol is carried out in the presence of the reaction gas resulting from the stage of oxidation of the propylene to give acrolein, use may be made of pure glycerol or of a concentrated aqueous glycerol solution, said reaction gas comprising steam. Preferably, the concentration of the aqueous glycerol solution ranges from 50% to 100%.

The glycerol can be injected in the liquid form or in the gas form. Injection in liquid form makes it possible to benefit from the latent heat of vaporization of the glycerol, thus making it possible to cool the gases resulting from the upstream stage of oxidation of the propylene. In this case, the dehydration catalyst can be preceded by a bed of inert materials over which the glycerol is vaporized. It can be injected in the gas form at a lower temperature than that of the gases exiting from the oxidation region, which makes it possible to further increase the effect of cooling these gases. Furthermore, the glycerol can be injected under pressure, so that the reduction in pressure of the gas makes possible a further consumption of heat.

The dehydration reaction of the glycerol is carried out in the presence of molecular oxygen, which occurs in the gas mixture feeding the reactor for the oxidation of the propylene or in the gas mixture resulting from the stage of oxidation of the propylene. The molecular oxygen can be present in the form of air or in the form of a gas mixture comprising molecular oxygen. According to one embodiment of the invention, it is possible to add an additional amount of molecular oxygen or of a gas comprising molecular oxygen for the stage of dehydration of the glycerol. The amount of oxygen is chosen so as to be outside the flammability range at all points of the plant. The presence of oxygen makes it possible to limit the deactivation of the dehydration catalyst by coking. Furthermore, the addition of oxygen improves the reaction yield for numerous catalytic systems.

The reaction for the catalytic oxidation of the propylene to give acrolein is carried out according to conditions known to a person skilled in the art by passing a gas mixture, which can comprise propylene, steam, an inert gas, which can be nitrogen or argon, and molecular oxygen or a gas comprising molecular oxygen, over a catalyst for the oxidation of the propylene. The oxidation reactor is generally a fixed bed multitubular reactor. The oxidation reactor can also be a plate exchanger with a modular arrangement of the catalyst, such as described in the documents EP 995 491, EP 1 147 807 or US 2005/0020851.

In the case where the catalytic oxidation of the propylene is carried out in the presence of a thermal ballast, such as described, for example, in the document EP 293 224 A1, which makes possible the use of a higher propylene flow rate, the gas mixture resulting from the reaction has a higher specific heat Cp. The process according to the invention is particularly advantageous in this case for discharging the excess heat transported by the reaction gases.

A preferred embodiment of the invention consists in using propane as inert gas as replacement in all or part for the nitrogen of the air. The propane, by virtue of its higher specific heat, carries more heat to the reactor, which makes it possible to more easily carry out the reaction for the dehydration of the glycerol. The gas resulting from the dehydration stage then comprises, as main constituents, steam, propane, acrolein and residual oxygen. After absorption of the acrolein, the gases rich in propane can be recycled. Preferably, the gas is subjected to purification treatments in order to remove impurities which may be harmful to the dehydration and oxidation reactions, such as CO and/or $CO_2$, and in order to limit the concentration of these impurities in the recycle loop. In this case, it is particularly advantageous to control the concentration of argon in the gas loop on account of its very low specific heat. Mention may be made, as separation techniques, which can be used alone or in combination, of the selective oxidation of CO to give $CO_2$, washing with amines, washing with potassium hydroxide, adsorption techniques, membrane separation or cryogenic separation.

With reference to FIG. 1, in a conventional process for the oxidation of propylene to give acrolein, a gas mixture 1 comprising propylene, steam, nitrogen and molecular oxygen is passed into a multitubular reactor from the top downward over a catalyst 2 for the oxidation of propylene. After cooling using a heat exchanger 8, a mixture 3 comprising the unreacted gases, the acrolein produced and byproducts is obtained. Liquid coolants circulate in 6 and 7, so as to maintain the reaction temperature which can be between 300° C. and 320° C. The heat exchanger 8 can be placed directly downstream of the catalytic bed, as in FIG. 1, or can be installed following the oxidation reactor.

Figure 2:
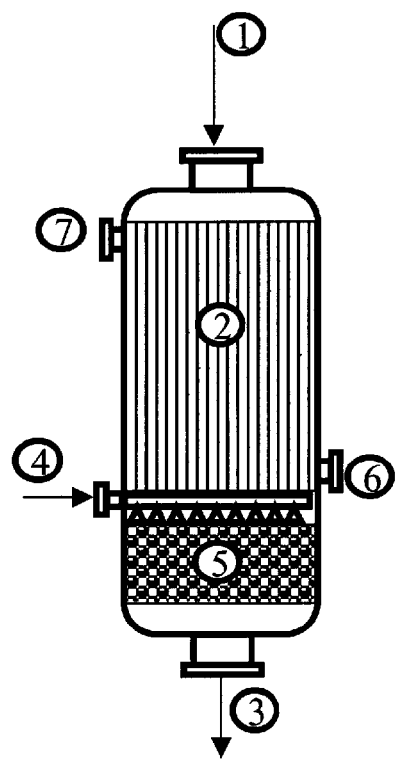

In accordance with a first embodiment of the process according to the invention, illustrated diagrammatically in FIG. 2, the heat exchanger 8 downstream of the bed of catalyst 2 for the oxidation of propylene is replaced (in all or in part) by a stage of dehydration of glycerol which consists in passing a mixture 4, composed of glycerol in the form of a vaporized aqueous solution and of oxygen, and at the same time as the gas mixture exiting from the oxidation region, over a catalyst 5 for the dehydration of glycerol. A mixture of acrolein, resulting both from the reaction for the oxidation of propylene and from the reaction for the dehydration of glycerol, and also the byproducts resulting from these two reactions, is obtained at the outlet.

Figure 3:
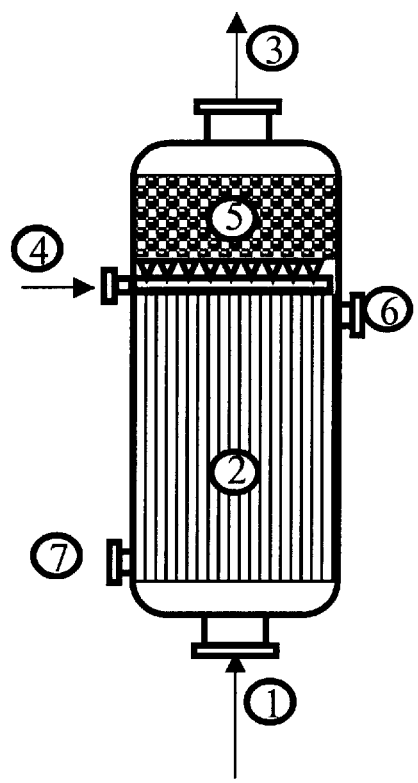

In accordance with a second embodiment of the process of the invention, illustrated diagrammatically in FIG. 3, the oxidation reactor is fed via the gas mixture 1 from the bottom upward, the catalyst 5 for the dehydration of glycerol occurring in this configuration at the top of the reactor. The changing of catalyst is thus facilitated. The bed of dehydration catalyst, which can be of conventional fixed bed type or in modules (sheets or pans), can be easily extracted and replaced. The regeneration of the catalyst can thus be easily carried out outside the reactor.

Figure 4:
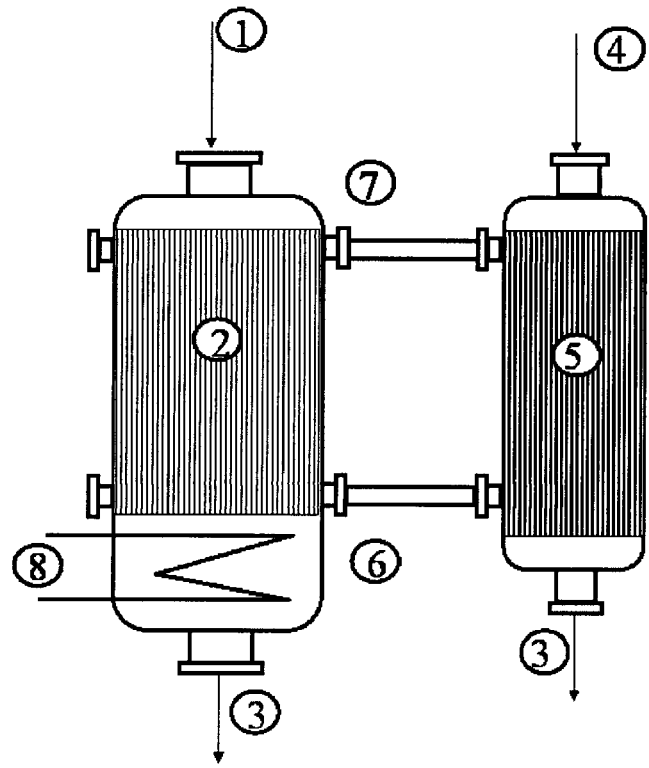

In accordance with a third embodiment of the process of the invention, illustrated in FIG. 4, the dehydration catalyst 5 is placed, in all or in part, in the boiler which is used to cool the heat-exchange fluid circulating in 6 and 7 and which removes the heat from the oxidation reaction by producing steam in the boiler.

As the endothermic dehydration reaction is carried out in part in the boiler, it is possible to remove more heat, which makes it possible indirectly to increase the propylene flow rate in the oxidation reactor and thus to simultaneously produce more acrolein via the oxidation of the propylene and via the dehydration of the glycerol. In this embodiment, it is preferable for the catalysts to operate in similar temperature ranges.

Figure 5:
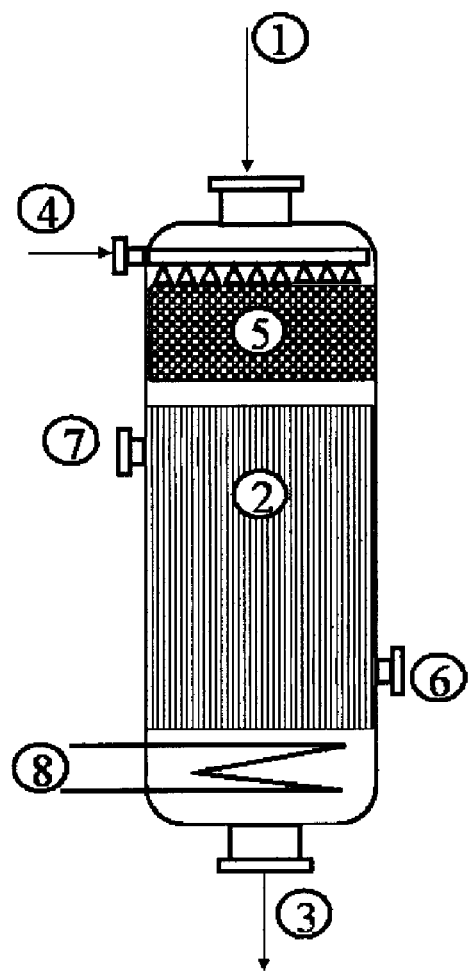

In accordance with a fourth embodiment of the process according to the invention, illustrated in FIG. 5, the catalyst 5 for the dehydration of glycerol is placed upstream of the catalyst 2 for oxidation of propylene. It is necessary in this case to heat the glycerol solution to a high temperature in order to vaporize it over the dehydration catalyst and in order to maintain the reaction gases at a sufficiently high temperature before entering the catalytic region for oxidation of propylene. The dehydration catalyst can be placed in modules or pans at the reactor top; it is thus easily changed when it is deactivated. The glycerol 4 can also be cofed with the gas mixture 1 comprising the propylene. The dehydration catalyst can be placed immediately above the bed of catalyst for the oxidation of propylene.

It is possible to envisage employing another endothermic reaction than that of the dehydration of glycerol in order to efficiently recover the heat from the oxidation reaction. In particular, the reaction for the oxydehydration of propane-1,3-diol or the dehydration of propan-1-ol or propan-2-ol are also advantageous in certain aspects, particularly if the bed of dehydration catalyst is placed upstream of the reactor for the oxidation of propylene to give acrolein. This is because the dehydration of propane-1,3-diol can result in allyl alcohol, which, in its turn, can be oxidized over the catalyst for the oxidation of propylene to give acrolein. Propan-1-ol or propan-2-ol can be dehydrated to give propylene and can subsequently be oxidized to give acrolein over the oxidation catalyst.

The following examples illustrate the present invention without, however, limiting the scope thereof.

In the examples, the products formed, acrolein and acrylic acid, are analyzed by chromatography on an EC-1000 capillary column attached to an HP6980 chromatograph equipped with an FID detector. Quantitative analysis is carried out with an external standard.

EXAMPLE 1

Use is made of a configuration such as represented in FIG. 5, in which the glycerol is cofed with the gas mixture comprising the propylene, and which comprises two catalyst beds.

Use is made of a pyrex reactor equipped with a sintered glass in order to retain the catalysts. A weight of 6.578 g of catalyst for the oxidation of propylene to give acrolein with the reference ACF7 (from Nippon Shokubai), diluted with 7 ml of silicon carbide with a particle size of 0.125 mm, is first of all charged. Subsequently, several beds of silicon carbide (SiC) are charged, so as to separate the two catalyst beds and to independently control their temperature: 2 ml with a particle size of 0.125 mm, then 7 ml with a particle size of 0.5 mm, then again 2 ml with a particle size of 0.125 mm and finally 1 ml with a particle size of 0.062 mm. Subsequently, a weight of 1.522 g of catalyst for the dehydration of glycerol with the reference Z1044 (tungstated zirconia from Dailchi Kigenso KK), diluted with 4 ml of silicon carbide with a particle size of 0.062 mm, is charged. The reactor is then made up to height with silicon carbide with a particle size of 0.125 mm (2 ml), 0.5 mm and then 1.19 mm.

The reactor is subsequently connected to the test plant. The temperatures of the two layers of catalyst are independently regulated at 260° C. for the upper dehydration layer and at 305° C. for the lower oxidation layer.

The reactor is fed via the top with a gas mixture of propylene/oxygen/helium-krypton/water-glycerol. The helium-krypton gas mixture comprises 4.92% of krypton, which acts as internal standard. The water-glycerol mixture comprises 30% by weight of glycerol.

The hourly molar flow rates (expressed in micromoles per hour) of the constituents of the mixture are as follows: 30089/55584/288393/water:53489-glycerol:4509. These conditions represent a total molar flow rate of $C_3$ compounds (propylene+glycerol) of 34598 micromol/h.

The effluents are collected at the outlet of the reactor via a cold trap comprising ice and the acrolein and the acrylic acid produced are quantitatively determined by chromatographic analysis.

The effluents are accumulated in the trap for a time of 82 minutes. The noncondensable gases are analyzed throughout the duration of the assessment. The amount of acrolein produced is 25302 micromol/h and the amount of acrylic acid is 2103 micromol/h.

EXAMPLE 2

Comparative

Example 1 is repeated but the aqueous glycerol solution is replaced with pure water. The molar flow rates in micromol/h of the reactants are then: propylene/oxygen/helium-krypton/water 30089/55584/288393/76666.

The effluents are accumulated in the trap for a time of 88 minutes. The noncondensable gases are analyzed throughout the duration of the assessment. The amount of acrolein produced is 20 391 micromol/h and the amount of acrylic acid is 1157 micromol/h.

EXAMPLE 3

Comparative

Example 2 is repeated but while replacing the dehydration catalyst with silicon carbide. The same feed conditions are used.

The effluents are accumulated in the trap for a time of 75 minutes. The noncondensable gases are analyzed throughout the duration of the assessment. The amount of acrolein produced is 20 821 micromol/h and the amount of acrylic acid is 1223 micromol/h.

EXAMPLE 4

Use is made of a configuration such as represented in FIG. 2, in which the glycerol is introduced over a dehydration catalyst at the same time as the gas mixture resulting from the region for the oxidation of propylene to give acrolein.

Use is made of a pyrex reactor provided with a sintered glass for retaining the catalysts. A weight of 1.538 g of dehydration catalyst with the reference Z1044 (tungstated zirconia from Dailchi Kigenso KK), diluted with 4 ml of silicon carbide with a particle size of 0.062 mm, is first of all charged. Subsequently, several beds of silicon carbide are charged, so as to separate the two catalyst beds and to independently control their temperature, and to make possible the injection of an aqueous glycerol solution or of hydrated glycerol between the two catalyst beds; 4 ml with a particle size of 0.125 mm, then 7 ml with a particle size of 0.5 mm and again 2 ml with a particle size of 0.125 mm are charged.

Subsequently, a weight of 6.522 g of catalyst for the oxidation of propylene to give acrolein with the reference ACF4 (from Nippon Shokubai), diluted with 7 ml of silicon carbide with a particle size of 0.125 mm, is charged. Finally, the reactor is made up to height with silicon carbide with a particle size of 0.125 mm (2 ml), 0.5 mm and then 1.19 mm.

The reactor is subsequently connected to the test plant. The temperatures of the two layers of catalyst are independently regulated at 260° C. for the lower dehydration layer and at 305° C. for the upper oxidation layer.

The reactor is fed via the top with a gas mixture of propylene/oxygen/helium-krypton/water with the following hourly molar flow rates (expressed in micromoles per hour): 30089/55584/288393/76666. The helium-krypton gas mixture comprises 4.92% of krypton, which acts as internal standard. A glycerol/water mixture comprising 80% by weight of glycerol is fed between the two catalyst beds with a flow rate of 4530/5794 micromol/h. These conditions represent a total molar flow rate of $C_3$ compounds (propylene+glycerol) of 34619 micromol/h.

The effluents are collected at the outlet of the reactor via a cold trap comprising ice and the acrolein and the acrylic acid produced are quantitatively determined by chromatographic analysis.

The effluents are accumulated in the trap for a time of 84 minutes. The noncondensable gases are analyzed throughout the duration of the assessment. The amount of acrolein produced is 25 852 micromol/h and the amount of acrylic acid is 1170 micromol/h. The residual propylene is 2895 micromol/h.

EXAMPLE 5

Example 4 is repeated but using a 95% by weight glycerol solution (hydrated glycerol).

The hourly molar flow rates (in micromoles per hour) of the constituents of the mixture are as follows: propylene/oxygen/helium-krypton/water 30089/55584/288393/76666 for the top feed and glycerol/water 8220/2205 micromol/h for the intermediate feed. These conditions represent a total molar flow rate of $C_3$ compounds (propylene+glycerol) of 38309 micromol/h.

The effluents are accumulated in the trap for a time of 84 minutes. The noncondensable gases are analyzed throughout the duration of the assessment. The amount of acrolein produced is 28 099 micromol/h and the amount of acrylic acid is 1237 micromol/h. The residual propylene is 2856 micromol/h.

EXAMPLE 6

Comparative

Example 4 is repeated but while replacing the dehydration catalyst with silicon carbide and while not introducing glycerol solution.

The effluents are accumulated in the trap for a time of 73 minutes. The noncondensable gases are analyzed throughout the duration of the assessment. The amount of acrolein produced is 22 373 micromol/h and the amount of acrylic acid is 1150 micromol/h. The residual propylene is 2933 micromol/h.

What is claimed is:

1. A process for the preparation of acrolein by oxidation of propylene, characterized in that it comprises a stage of dehydration of glycerol in the presence of a propylene-comprising gas.

2. The process as claimed in claim 1, characterized in that the propylene-comprising gas is the reaction gas resulting from a stage of oxidation of propylene to give acrolein.

3. The process as claimed in claim 1, characterized in that the propylene-comprising gas is a gas mixture which feeds a reactor for the oxidation of propylene.

4. The process as claimed in claim 1, characterized in that the dehydration is carried out in the gas phase in the presence of a catalyst.

5. The process as claimed in claim 1, characterized in that molecular oxygen is added for the stage of dehydration of the glycerol.

6. The process as claimed in claim 1, characterized in that the glycerol is injected in the liquid form or in the gas form.

7. The process as claimed in claim 1, characterized in that use is made of pure glycerol or glycerol in the form of a concentrated or dilute aqueous solution.

8. The process as claimed in claim 1, characterized in that the oxidation of the propylene is carried out in the presence of a thermal ballast.

9. The process as claimed in claim 1, characterized in that the stage of dehydration of the glycerol is carried out in part in a boiler which is used to cool a heat-exchange fluid.

* * * * *